United States Patent [19]

Goldsmith

[11] 4,365,200
[45] Dec. 21, 1982

[54] SELF ALARMING FOUR DOUBLE ELECTRODES CONDUCTIVITY CELL

[75] Inventor: Herbert Goldsmith, Rockville, Md.

[73] Assignee: Chemed Corporation, Cincinnati, Ohio

[21] Appl. No.: 167,896

[22] Filed: Jul. 14, 1980

[51] Int. Cl.³ ............................................ G01N 27/42
[52] U.S. Cl. ..................... 324/449; 324/444
[58] Field of Search ........................ 324/446, 444, 449

[56] References Cited

U.S. PATENT DOCUMENTS

| | | | |
|---|---|---|---|
| 3,774,105 | 11/1973 | Henning | 324/449 |
| 3,947,329 | 3/1976 | Segl | 324/444 |
| 4,275,352 | 6/1981 | Sudar | 324/449 |

FOREIGN PATENT DOCUMENTS 936045  9/1963  United Kingdom ................ 324/449

*Primary Examiner*—Michael J. Tokar
*Attorney, Agent, or Firm*—Browdy and Neimark

[57] ABSTRACT

A liquid conductivity cell utilizing the Kelvin four-electrode system, and a circuit to operate an alarm when the operating electrodes have reached a predetermined state of fouling. Thus, the invention cell self alarms when the electrodes have fouled. The electrodes each have two flow passageways, whereby the liquid takes a "U" shaped path, and whereby the outer electrode closest to the liquid inlet and outlet fittings sinks all stray currents and the like to thereby permit interference free operation.

10 Claims, 4 Drawing Figures

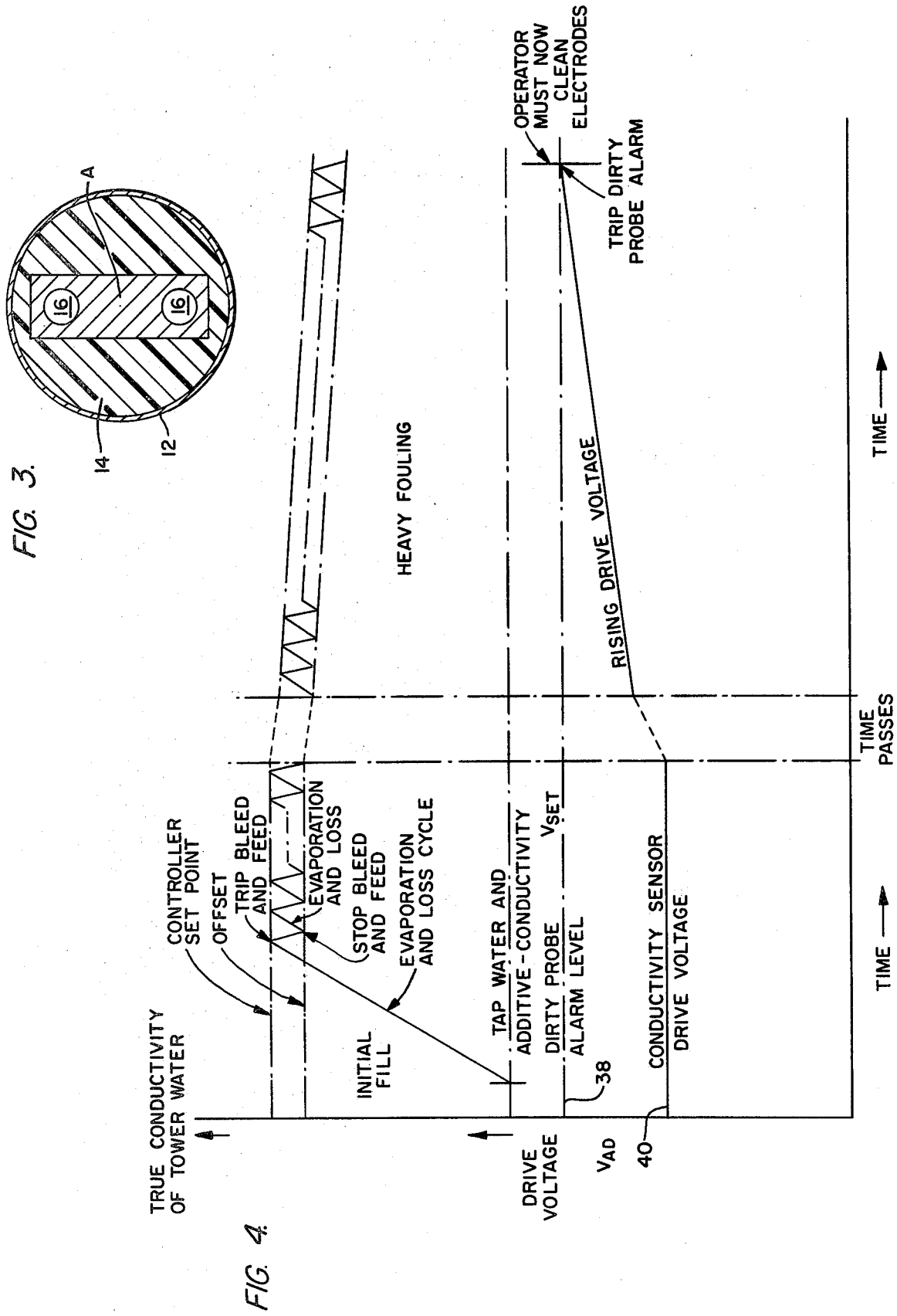

SELF ALARMING FOUR DOUBLE ELECTRODES CONDUCTIVITY CELL

This invention relates to cells for measuring the electrical conductivity of liquids. Conductivity is proportional to salinity, acidity, entrained solids, and other useful parameters of liquids. Applications for the invention include the monitoring of the conductivity of boiler water, monitoring the conductivity of human blood in various medical applications, and monitoring the conductivity of solutions used in the chemical and biochemical industries.

More particularly, the invention pertains to such cells comprising a body of electrical insulating material defining a bore through which the liquid flows. The electrodes of the invention are embedded into the dielectric material defining the bore, thus forming part of the surface of the bore to be contacted by the flowing liquid.

The invention comprises a set of four such annular electrodes, the outer zones of which are current or drive electrodes and are connected to a low impedance source of electrical power. The inner electrodes are connected to a high impedance amplifier, and are thus the voltage electrodes. They respond to the input drive power with a voltage as driven by the current electrodes and as modified by the conductivity of the flowing liquid. This Kelvin type cell is well known in the prior art, see for example, U.S. Pat. No. 3,993,945 to Warmoth.

An important advantage of the invention is obtained by the so called "folded" nature of the flow path through the cell. This is accomplished by providing that the set of four electrodes each has two flow passages, and providing that flow through the cell is in a "U" shaped path. This is done by providing the inlet and outlet fittings for the fluid generally at a radial plane in a generally cylindrical cell to one side of the array of four electrodes. Liquid goes in the inlet fitting, across the first row of aligned openings through the four electrodes, (which could be considered the upper openings of the electrodes), around a "U" or return portion, and then back out through the "lower" row of openings in the aligned electrodes. Thereafter, the liquid exits the cell through the other fitting which is in the same general radial plane as the inlet fitting. The last electrode in the array furthest from the fittings is arranged in the circuit of the invention so that it is essentially grounded through a circuit component.

In this manner, the necessity for a fifth guard electrode, as mentioned in the above identified Warmoth patent, as well as is used in a companion patent application entitled "Self Alarming Five Single Electrodes Conductivity Cell" by Goldsmith and Stillwell, filed on July 14, 1980, as Ser. No. 167,897, and assigned to the same assignee as the present invention, is eliminated.

The outer shell of the cell may be a metallic conductor which is connected electrically by ground pins to the aforementioned fittings which are also metallic. These fittings may be so configured that their ends protrude slightly into the bores through which fluid flows. The combination of shell, ground pins and fittings then comprise an "electrode" which can be grounded to eliminate leakage currents.

Further, since this outermost electrode is a ground, then, particularly in medical applications, patients and users of the invention are protected against possible injury due to leakage coming from the measuring system.

The invention is operated in a constant voltage mode. In operation, power is driven into the outer current electrodes from an oscillator. The voltage measured across the inner voltage electrodes is dependent only upon the sensed current from this oscillator and the conductivity of the liquid in the cell. The voltage detected as the voltage electrodes is provided to a differential amplifier where it is compared with a reference signal. The output signal from this amplifier operates the oscillator driving the current electrodes so as to maintain the voltage at the middle voltage electrodes at a predetermined constant voltage. As fouling occurs, the input current needed to maintain the voltage at the voltage electrodes current increases. In all cases, the current sensed by the current to voltage converter is directly proportional to the conductivity of the liquid, and this current is used to drive a direct reading conductivity meter.

As fouling occurs at the current electrode surfaces within the cell contacting the liquid, which results in additional resistance thereat, the voltage at the voltage electrodes will remain unaffected since even if the voltage electrodes foul, the current passing through these electrodes is so low due to the high impedance of the differential amplifier to which they are connected, that any surface voltage drop will be insignificant, assuring that the current is correct for a particular value of conductivity even though the voltage across the current electrodes may increase due to this increased resistance arising from the fouling of the electrodes.

By providing an alarm to be operated by this increased power supplied to the current electrodes at a predetermined level, which is provided by an additional adjustable set point voltage, the invention conductivity cell will alarm on its own when cleaning due to fouling is required.

This has been substantial problem in the prior art because the fouled or unfouled condition of the electrodes is difficult to determine. In industrial applications, in order to assure proper operation, the cell was periodically cleaned on a regular basis regardless of its condition, because the fouled or unfouled condition of the electrodes is difficult to determine. This caused a substantial waste of manpower, wasted down time, and the like for the cleaning when the cleaning was not necessary. More importantly, cleaning might have been required earlier, and thus the cell produced erroneous results during the time the fouling had increased to an undesirable operation impairing level. In medical applications, human life is at stake and high reliability is a prime criterion. Thus, the alarming feature is even more important, indicating to the nurses and other users of the equipment that the instrument needs to be serviced. The invention is contemplated particularly for use with kidney dialysis machines.

In addition, the invention circuit will output a reading for conductivity and means are provided to temperature correct this reading so that it is accurate as an absolute value regardless of the temperature of the liquid being measured.

The invention also provides a ground means at the liquid inlet and outlet fittings to ground any stray currents which might enter the system via that route. If these fittings are poorly grounded within the external electrical power distribution system, any currents generated will be absorbed by the current drive electrode-oscillator combination whose low impedance and current sinking capabilities nullifies the effect of these currents upon the measuring system.

The above and other advantages of the invention will be pointed out or will become evident in the following detailed description and claims, and in the accompanying drawings also forming a part of the disclosure, in which:

FIG. 3 is a cross-sectional view taken on line 3—3 of FIG. 1; and

FIG. 4 is a chart to illustrate its operation.

Figure 1:
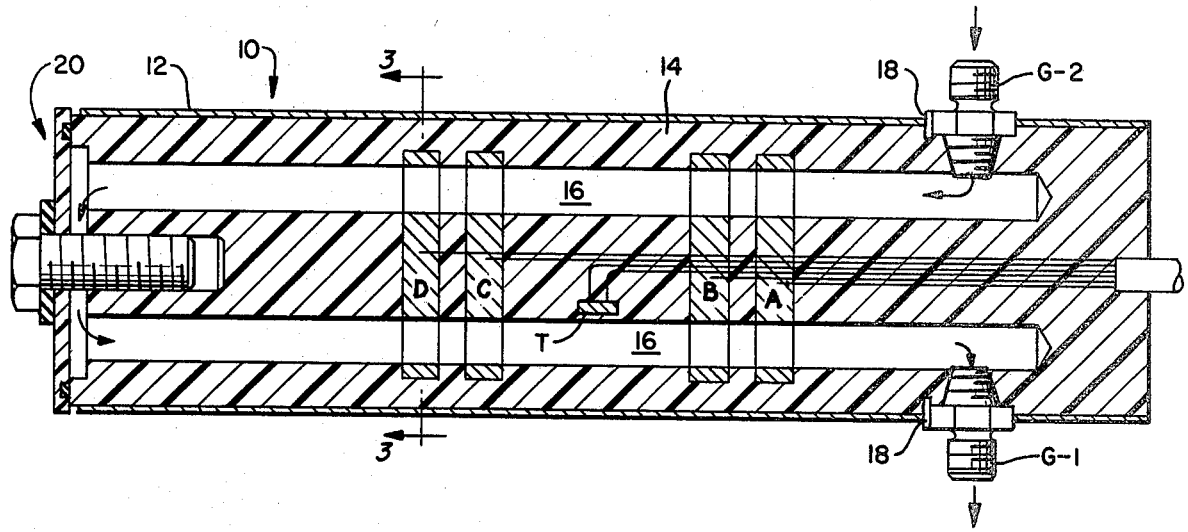
FIG. 1 is a cross-sectional elevational view of a cell embodying the invention.

Referring now in detail to the drawings, 10 indicates a conductivity cell embodying the invention. Cell 10 comprises an outer tube 12 which is filled with epoxy or the like dielectric material 14. A set of four electrodes A, B, C, and D, are embedded in the dielectric material 14 as shown, and their wires are run through the material 14 as indicated. Bores 16 may be symmetrically disposed on either side of the center of the cell 10 and may lie in the same radial plane. The open ends of bores 16 communicate with a larger space arranged concentrically with the center of the cell 10. The bores 16 together with this space comprises the single "U" shaped fluid flow passageway of the invention. A thermistor T is located in close proximity to but not directly in contact with the fluid flow path 16 to sense temperature. A pair of side conduits extend out from the bore 16 and fittings G-1 and G-2 are provided to allow flow through the cell, as indicated by the arrows. Ground pins 18 are provided for cooperation with the metal tube 12 and fittings G-1 and G-2 to provide a better ground for stray currents that might enter through the pipes, conduits etc., with which cell 10 is used. The fittings G-1 and G-2 may be so located that their pipe threaded ends protrude slightly into the bores 16, respectively. The open end of the larger space is closed off by an assemblage 20 of a sealing end plate, insulating screw and an insulating washer, removal of which permits cleaning of the inside of the bore 16 and the ends of the fittings G and G$_2$. All of the parts of assemblage 20 are non-electrical conducting.

Referring to FIG. 3, the shape of electrode A, which is the same as electrodes B, C and D, is shown. The return portion between the upper and lower bores 16 to complete the through channel is through the space provided by the configuration of the dielectric material 14 in the vicinity of the end cap assemblage 20, all as is indicated in FIG. 1 and the arrows thereon.

Figure 2:
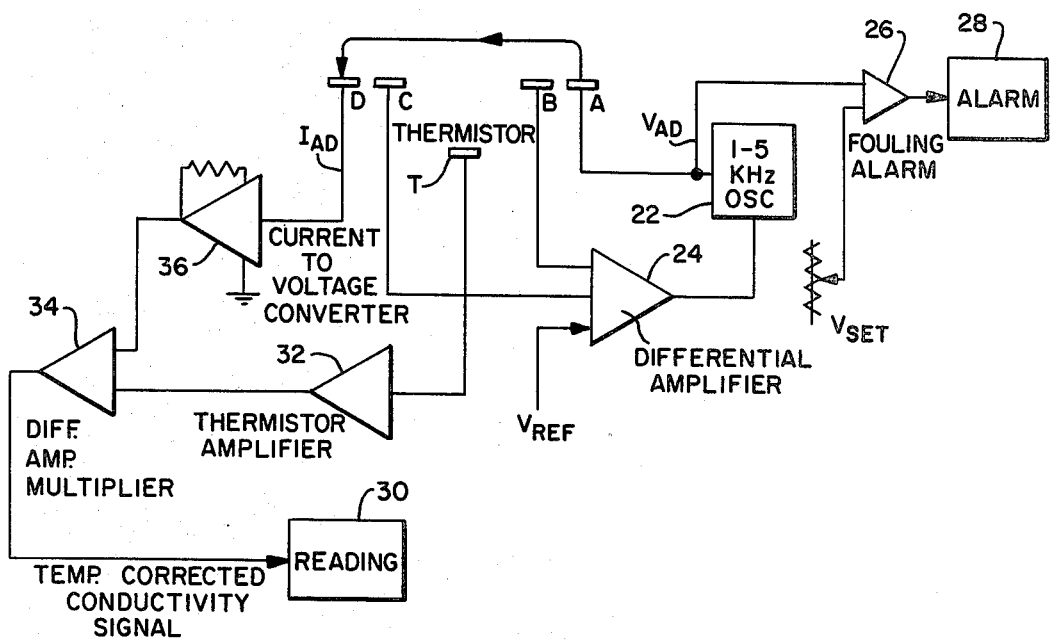
FIG. 2 is an electrical schematic diagram.

Referring now to FIG. 2, the outer electrodes A and D are the current of driving electrodes, and electrodes B and C are the driven or voltage electrodes, the voltage at which is kept constant to achieve the constant voltage mode of operation with its attendant advantages as set forth above.

This can be stated mathematically:

$$I_{AD} = V_{BC} G_{SOL} K \qquad \text{eq. (1)}$$

$$I_{AD} = (V_{AD}/R_{SY}) \qquad \text{eq. (2)}$$

$$V_{AD} = V_{BC} G_{SOL} R_{SY} k \qquad \text{eq. (3)}$$

where k is a constant dependent upon the geometry of the cell.

Equation 1 states that the resistance of the solution, the inverse of which is its conductivity G, times the voltage at BC, times the constant k, equals the current sensed at electrode D. This is in accordance with Ohm's Law, and is the basic premise of the Kelvin system wherein the outer are the current electrodes and the inner are the voltage electrodes, with the solution being the connecting medium.

In eq. (2) the current sensed at the current electrode D is seen to be equal to the voltage at the AD electrodes divided by $R_{SY}$, the resistance of the current path form electrode A to D and which is also responsive to the fouling of the electrodes A and D. That is, $R_{SY}$ increases as the electrodes foul.

By dividing eqs. (1) and (2) by each other and rearranging one comes to eq. (3) which says that if $V_{BC}$ is held constant, then the voltage at the current electrodes will respond to both the conductivity of the solution and the resistance of the system. If liquid conductivity holds steady, as in a steady state condition, then $V_{AD}$ will respond to the fouling of the electrodes. Similarly, with $V_{BC}$ held constant $V_{AD}$ will also respond to a change in conductivity, it being assumed that the fouling occurs slowly and not at one time. Thus, $V_{AD}$ responds to both $R_{SY}$ which is indicative of electrode fouling, as well as the solution conductivity. This is fortuitous, since a high value of $G_{SOL}$ indicates a large burden of dissolved solids, with a high probability for the formation of fouling precipitates, and this increases the sensitivity of $V_{AD}$ to any increase in the value of $R_{SY}$ due to fouling.

Eq. (3) underlies the modus operandi of the invention. It should be noted that $I_{AD}$ drops out in the mathematics, and thus in the real cell that it is a nonimportant parameter as to the self alarming feature. However, $I_{AD}$ is proportional to conductivity generally, and is used to drive meter 30, as described in detail below.

Referring now to FIG. 2, a low impedance oscillator 22 drives the current electrode A under the control of and via the feedback from a high impedance differential amplifier 24. The voltage $V_{BC}$ picked up at the voltage electrodes is delivered to the amplifier 24 wherein it is compared to a reference voltage $V_{REF}$, and the output is used to drive the oscillator 22. The output of the oscillator 22, which is $V_{AD}$, is also provided to a comparator 26 which drives suitable alarm means 28. A predetermined set voltage $V_{SET}$ is also provided to the comparator 26, and when $V_{AD}$ equals $V_{SET}$ then the comparator 26 will activate the alarm 28. The alarm 28 can take any form well known to those skilled in the various arts to which the invention pertains.

The circuit of FIG. 2 also provides means to drive an output reading device 30 which can comprise a meter graduated directly in units of conductivity or the like of the liquid. That is, the alarm means 28 which is an important advance of the invention is coupled with a conventional direct readout of conductivity or some other parameter in units of that parameter.

To this end, the signal from the thermistor T is provided to an amplifier 32 and from there to a differential amplifier 34. The second input to amplifier 34 is $I_{AD}$ via a current to voltage converter 36. The conversion performed at the device 36 is necessary because of the particular circuit used, which is a voltage responsive circuit and the current $I_{AD}$ is the parameter which is proportional to the conductivity of the solution being measured, as indicated by eq. (1) above, $V_{BC}$ being held constant as set forth above.

In this manner, the output of the differential amplifier 34 comprises a temperature corrected conductivity signal, in direct proportion to $I_{AD}$, which is used to drive the meter 30 in the usual manner.

Referring now to FIG. 4, line 38 corresponds to the set voltage $V_{SET}$ which is the predetermined value at which the alarm means 28 are to be activated in response to a predetermined amount of fouling at the electrodes A, B, C and D. The line 40 corresponds to $V_{AD}$ which is the drive voltage producing $I_{AD}$ driving the conductivity cell circuit. As this voltage rises it will both operate the alarm when it reaches the line 38, and operate the meter 30 during normal operation prior that time.

The upper part of FIG. 4 indicates an application such as a typical tower controller which maintains the cooling-water conductivity within controlled limits. As the water evaporates the dissolved solids concentration and the conductivity increases. When this conductivity reaches a given set point, the cooling water is drained while at the same time tap water is admitted, thus lowering the conductivity to the desired value.

While the invention has been described in detail above, it is to be understood that this detailed description is by way of example only, and the protection granted is to be limited only within the spirit of the invention and the scope of the following claims.

We claim:

1. A conductivity cell comprising a pair of voltage electrodes arranged within a pair of current electrodes, with all of said electrodes being arranged seriatim in the direction of flow through the cell, each of said electrodes comprises at least two flow openings, all four of said electrodes being arranged in said cell with their openings in such relation to each other so as to thereby define two flow passageways in said cell, means to connect said two passageways into flow communication with each other to thereby define a single "U" shaped flow passageway through said cell, said single "U" shaped passageway thereby having a functional length equal to about twice the length of said cell, said single "U" shaped passageway passing through each of said electrodes at least twice via said at least two openings in each of said electrodes, means to permit flow into and out of said cell, and said flow permitting means being located in said cell in spaced relation to said passageway connecting means to said electrodes.

2. The cell of claim 1, alarm means, and an electrical circuit for utilizing the power provided to said current electrodes which increases as said electrodes progressively foul during use of the cell to operate said alarm means to indicate a predetermined condition of fouling of said electrodes.

3. The combination of claim 1, wherein said voltage electrodes are operated in a constant voltage mode with their voltage being held at a predetermined constant value, whereby the voltage of the power supplied to said current electrodes increases as said electrodes progressively foul, and using the supply voltage to operate said alarm means when said supply voltage exceeds a predetermined value, said last mentioned predetermined value corresponding to a predetermined condition of fouling of said electrodes.

4. The combination of claim 3, said means to use said supply voltage to operate said alarm means comprising a comparator, and means to supply said predetermined voltage and the supply voltage to said current electrodes to said comparator.

5. The combination of claim 1, said cell being of generally tubular configuration, and said passageway connecting means being located at one end of said cell.

6. The combination of claim 5, and said passageway connecting means being combined with end non-electrical conducting cap closure means for said cell at said one end of said cell.

7. The combination of claim 5, said flow permitting means comprising a pair of fittings located substantially in a common radial plane of said tubular cell, and said fittings being located at the end of said array of four electrodes remote from said passageway connecting means.

8. The combination of claim 7, said fittings comprising metallic grounded fittings, the ends of said fittings protruding slightly into said passageways, whereby the ends of said fittings are cleaned simultaneously when said passageways are cleaned.

9. A conductivity cell comprising a pair of voltage electrodes arranged within a pair of current electrodes, with all of said electrodes being arranged seriatim in the direction of flow through the cell, each of said electrodes comprises at least two flow openings, all four of said electrodes being arranged in said cell with their openings in such relation to each other so as to thereby define two flow passageways in said cell, means to connect said two passageways into flow communication with each other, means to permit flow into and out of said cell, and said flow permitting means being located in said cell in spaced relation to said passageway connecting means and to said electrodes, and wherein said voltage electrodes are operated in a constant voltage mode with their voltage being held at a predetermined constant value, whereby the voltage of the power supplied to said current electrodes increases as said electrodes progressively foul, and using the supply voltage to operate said alarm means when said supply voltage exceeds a predetermined value, said last mentioned predetermined value corresponding to a predetermined condition of fouling of said electrodes.

10. The combination of claim 9, said means to use said supply voltage to operate said alarm means comprising a comparator, and means to supply said predetermined voltage and the supply voltage to said current electrodes to said comparator.

* * * * *